United States Patent [19]
Evans

[11] Patent Number: 5,085,996
[45] Date of Patent: Feb. 4, 1992

[54] MICROORGANISM GROWTH ACCELERATION MEDIUM CONTAINING AN EFFECTIVE AMOUNT OF PICOLINIC ACID OR METAL PICOLINATE TO PROMOTE GROWTH OF THE MICROORGANISM

[76] Inventor: Gary W. Evans, Route 1, County Rd., 13 Box 86-B, Puposky, Minn. 56667

[21] Appl. No.: 595,031

[22] Filed: Oct. 9, 1990

Related U.S. Application Data

[62] Division of Ser. No. 07/225,977, Jul. 29, 1988.

[51] Int. Cl.$^5$ .......................... C12N 1/38; C12N 1/32; C12R 1/19; C12R 1/865
[52] U.S. Cl. .................................. 435/244; 435/252; 435/849; 435/942
[58] Field of Search ............... 435/244, 252, 849, 942

[56] References Cited

U.S. PATENT DOCUMENTS

| | | |
|---|---|---|
| 2,320,478 | 6/1943 | Sperti . |
| 2,359,521 | 10/1944 | Harrison . |
| 3,476,647 | 6/1969 | Ushioda et al. . |
| 3,966,553 | 6/1976 | Charpentier . |
| 4,315,927 | 2/1982 | Evans . |
| 4,438,099 | 3/1984 | Azzariti . |

OTHER PUBLICATIONS

*Present Knowledge in Nutrition* 5th Ed. p. 571 (1984).
Kaplan, J., *J. Arch. Surg.* 119; pp. 1005-1008 (1984).
Goodson. W. et al., *J. Surg. Res.* 21:125-19 (1976).
*U.S. Federal Reg.* 3:151 (1978).
Gollakota, K., *J. Bacteriol.* 79:1-8 (1960).
Mirsky, N., et al., *J. Inorg. Biochem.* 13:11-21 (1980).
Chem. Abst. 90:1012a Jan. 1, 1979, Tanegashima et al., No. 1. Mukogawa Joshi Daigaku Kiyo 1977, 25, 15-23.
Chem. Abst. 71: 28095z Aug. 18, 1969, No. 7. Upreti et al. Biochem. Biophy. Res. Commun. 1969, 35(5) 611-618.
Chem. Abst. 101:21962j, vol. 101, No. 3, Jul. 16, 1984, Lie et al., Proc. Congr. Eur. Brewing Conv., 1983, 19th, 145-151.

*Primary Examiner*—Herbert J. Lilling
*Attorney, Agent, or Firm*—Knobbe, Martens, Olson & Bear

[57] ABSTRACT

A method, and composition suitable for use therein, which produces enhanced microorganism growth in vitro. The microorganism, for example fungi (e.g. yeast) or bacteria cells, is cultured in a medium containing an exogenously added growth promoter selected from picolinic acid and a metal picolinate, most preferably selected from picolinic acid, chromic tripicolinate and zinc dipicolinate. The method is applicable both to eukaryote and prokaryote cells.

6 Claims, 4 Drawing Sheets

MICROORGANISM GROWTH ACCELERATION MEDIUM CONTAINING AN EFFECTIVE AMOUNT OF PICOLINIC ACID OR METAL PICOLINATE TO PROMOTE GROWTH OF THE MICROORGANISM

This application is a division of application Ser. No. 225,977 filed July 29, 1988 now U.S. Pat. No. 4,997,765.

FIELD OF THE INVENTION

This invention relates to microbes and, particularly, to a method and composition which can produce enhanced microorganism growth (i.e. cell multiplication).

TECHNOLOGY REVIEW

Microorganisms such as yeasts and bacteria, have long been cultured in the production of desired products. In a typical culturing procedure for yeast or bacteria cells, the cells are placed in a medium containing an energy source such as a sugar or polysaccharide, along with required inorganic nutrients. Preferably, a "complete" medium is used, that is, one which also provides the essential amino acids or alternate nitrogen sources in order to enhance cell growth.

Known processes in which yeasts are cultured, include fermentation processes for the production of foodstuffs, such as alcoholic beverages, breads, yeast mass and yeast derivatives. Other fungi have also been cultured for some time for the purpose of producing antibiotics, organic acids, enzymes and food-flavor modifiers. Likewise, the culturing of bacteria is well known for the preparation of foodstuffs, such as cheese, fermented milk products, pickles and sauerkraut. Bacteria are also used for the preparation of enzymes for food and feed applications and the production of amino acids, antibiotics, pigments and vitamins. More recently, as a result of advances in DNA technology, microorganisms have become particularly important both in the production of a wide range of pharmaceutical products expressed from microorganisms harboring a recombinant DNA, as well as for experimental purposes relating to the study of DNA and related processes. Applications of various microorganisms are described by Peppler and Perlman, eds. "MICROBIAL TECHNOLOGY", Vol. 1 and 2, 1979, Academic Press, New York. Thus, it is apparent that means for enhancing microorganism growth rates would be advantageous in a wide variety of commercial and laboratory applications.

It is known that trace amounts of various elements are critical to many biochemical and physiological processes. For example, many metals participate in enzymatic catalysis through substrate binding, activation of enzyme-substrate complex, or by forming tight coordination complexes (i.e., metallo-enzymes). The necessity of adequate quantities of various heavy metals, and the physiology of metals, is discussed in U.S. Pat. No. 4,315,927 to Evans. That patent, and all other references cited herein, are incorporated by reference. The Evans patent also discloses the administration to mammals of metal picolinates, which are coordination complexes of the general formula: in which formula M represents the metallic cation and N is equal to the cation's valence. The patent provides particular examples of administration of zinc, copper, iron and chromium picolinates to mammals.

Picolinic acid (pyridine-2-carboxylic acid) is a known compound which is an isomer of nicotinic acid. In addition, it is known that brewers yeast contains chromium in a form which is assimilated at a far higher rate than inorganic chromium or chromium in other foodstuffs (see "Present Knowledge In Nutrition", Fifth Edition, The Nutrition Foundation, 1984, at pg. 571). Furthermore, beneficial effects of extracts from bakers or brewers yeast, which are both included under the technical name *Saccharomyces cerevisiae*, have also been described. For example, U.S. Pat. No. 2,320,478 to Sperti discloses an alcohol extract of bakers yeast which improved skin respiration (i.e., the taking up of oxygen by the skin). Likewise, yeast cell extracts have been indicated as useful in promoting skin healing. See, for example, Kaplan, *Arch. Surg.*, Vol. 119 (September 1984); Goodson et al., *Journal of Surgical Research*, Vol. 21, p. 125 (1976); U.S. *Federal Register*, Vol. 3. No. 151 (Aug. 4, 1978). Similarly, U.S. Pat. No. 4,438,099 to Azzariti discloses a spray of *Candida kruseii* for use in healing of a burn and regeneration of burned skin. Gollakota, et al., *J. Bacteriol.*, Vol. 79, p. 1 (1960) demonstrated that α-picolinic acid (which is often referred to herein as simply 'picolinic acid'), at a concentration of $1.2 \times 10^{-3}$ molar ("M"), could inhibit sporulation of the bacteria, *Bacillus cereus* type T, with a minimum concentration to inhibit sporulation being $8 \times 10^{-4}$ M. Gollakota et al., also state that there was no significant difference in growth between a culture of *Bacillus cereus* containing such amounts of picolinic acid, and a control culture with no added α-picolinic acid.

SUMMARY OF THE INVENTION

The present invention provides a method for producing enhanced microorganism growth in vitro, which takes advantage of the fact that picolinic acid and metal picolinates have now been found to enhance microorganism growth in vitro. By "enhanced" growth in the foregoing context, is meant that the growth rate is greater in a medium conducive to growth of the microorganism, when the growth promoter is present, than it otherwise would be under the same conditions with the growth promoter absent.

The method of the present invention comprises producing enhanced microorganism growth in vitro by growing the microorganism in a culture medium which contains an exogenously added growth promoter selected from picolinic acid and a metal picolinate. "Exogenousl added" indicates that the material referred to has been provided in the culturing medium from a source other than the microorganism or microorganisms being cultured.

Of the metal picolinates which may be used, chromic ($Cr^{+3}$), zinc, iron, and manganese picolinates are preferred. Chromic tripicolinate and zinc dipicolinate are the most preferred. The amount of the growth promoter added may be adjusted in view of the particular organism being cultured and the culturing medium, in order to obtain enhanced microorganism growth. Preferably the amount of growth promoter present is at least 0.1 nanograms ("ng") of picolinate per milliliter ("ml") of culturing medium. It will be recognized though, that most compounds have a concentration at which they become toxic depending upon the compound and the microorganism. In the present case it is anticipated that the preferred upper limit of growth promoter concentration, will be about 80 μg of picolinate per ml, and most preferably about 10 μg per ml. By "picolinate" in this context, is meant the picolinate anion either of the metal picolinate complex, or the corresponding portion of picolinic acid whether or not the acid may be dissociated. It will be appreciated of course, that the picolinic acid may be partially dissociated in the medium. Further, the total amount of picolinic acid in solution includes both dissociated and undissociated forms, so that "picolinic acid" allows for adding to a solution a picolinate compound which would produce free picolinate ions in water.

Particular microorganisms the growth of which can be enhanced by the present invention include yeast and bacteria and, in particular, the yeast *Saccharomyces cerevisiae* and the bacterium *Escherichia coli* ("*E coli*").

The method of the present invention may include as an additional step the preparation of a culture medium for the microorganism by combining a microorganism nutrient medium (such as a medium containing a suitable saccharide) with a growth promoter of the compositions described so as to enhance the microorganism growth in the culture medium. The present application further includes compositions having no substantial quantity of active microorganisms, suitable for use in the methods described above, which include a microorganism nutrient (e.g., a saccharide such as a sugar, starch or cellulose, and optionally, amino acids), and a growth promoter of any of the compositions described above. Where yeasts or bacteria are to be grown, the added microorganism nutrient is preferably a saccharide.

DRAWINGS

Embodiments of the invention will now be described, with reference to the drawings in which.

DETAILED DESCRIPTION OF EMBODIMENTS OF THE INVENTION

A number of experiments were performed, to illustrate the action of picolinic acid and metal picolinates as growth promoters.

1. Growth In Deficient Liquid Media

In one series of experiments, an isolated pure culture of commercial bakers yeast (available under the trademark "RED STAR BRAND" from Universal Foods Corp., Milwaukee, Wis., U.S.A.) was grown in a complete agar medium sold under the trademark "DIFCO, YM" (available from Difco Inc., Detroit, Mich., U.S.A.), and transferred to a deficient liquid growth medium which is described by Mirsky, et al., *J. Inorg. Biochem.*, Vol. 13, p. 11, (1980). The deficient medium is free of amino acids and trace metals, and contains 2% glucose, vitamins and minerals (i.e., Ca, Mg) necessary for growth. Media produced by Difco, Inc. are described in "Difco Manual, Culture Media and Reagents for Microbiology," 10th edition, published by Difco Laboratories, Detroit, Mich., U.S.A. (1984). The pure yeast culture was then grown in the deficient medium and the harvested cells were then resuspended in a series of 25 ml aliquots of the deficient medium to produce in each aliquot a culture with a starting yeast concentration of about $5.5 \times 6.0 \times 10^6$ cells/ml. A control culture received no growth promoter while other samples received chromic tripicolinate growth promoter in an amount which produced a final concentration of between 1 and 80 ng/ml of picolinate. The cultures were then grown at 30° C. with continuous shaking for five hours, the cell population was counted again, and the growth increase calculated according to the formula:

Growth Increase=(final cell concentration minus initial concentration) divided by initial cell concentration.

Figure 1:
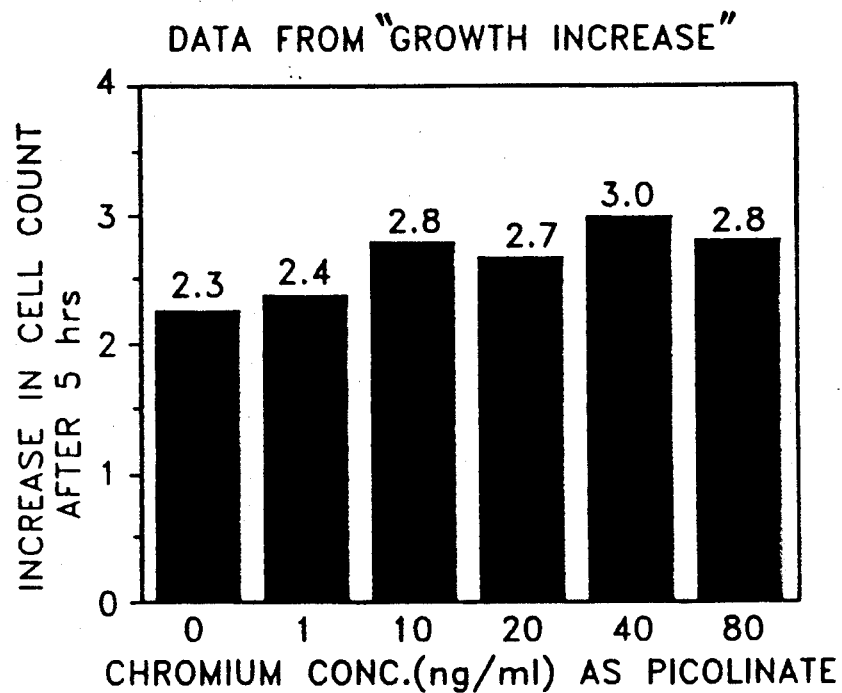
FIG. 1 illustrates the increase in growth of a yeast, in a deficient nutrient medium, with various amounts of exogenously added chromic tripicolinate.

"Growth Increase" is sometimes referred to herein as an increase in cell number or count, and may be expressed as a number or a percentage. The experiments were repeated a number of times to ensure reproducibility, and the mean results from both the control and the other cultures are plotted as indicated in FIG. 1. It will be seen from FIG. 1 that in comparison to the control, the addition of the growth promoter chromic tripicolinate in concentrations of 10 to 80 nanograms per ml ("ng/ml"), as picolinate, increased the growth rate of the yeast cells by between about fifteen to thirty percent.

Figure 2:
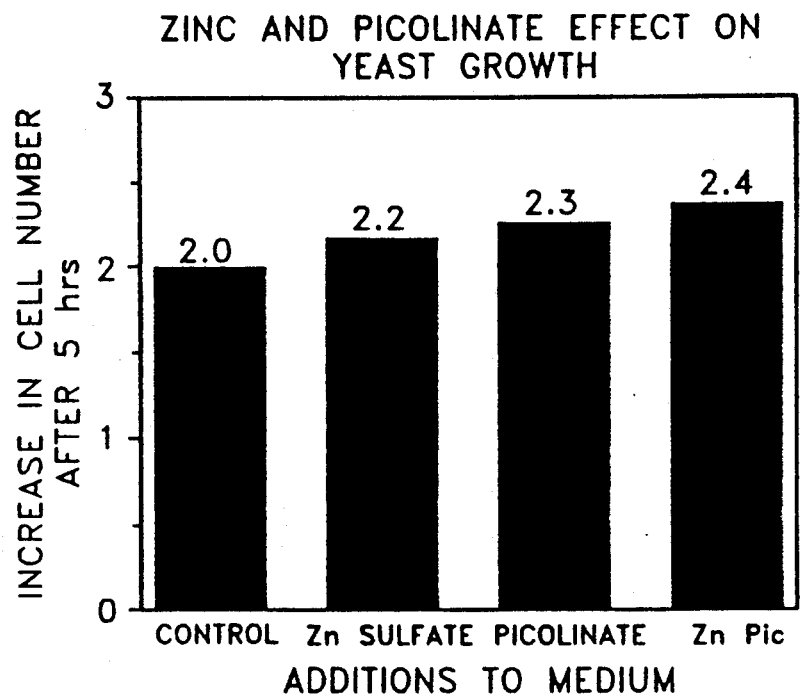
FIG. 2 illustrates the effect of growing the yeast with various growth promoters of the present invention, or with an inorganic salt or no additional additive.

Another series of experiments was performed using the same conditions as those just described but with the following exceptions. First, the initial yeast concentration in each sample was between 5.5 to $6.0 \times 10^7$ cell/ml. In addition, in one sample 50 ng of zinc per ml (as zinc sulfate) was added, while to other samples 250 ng/ml picolinic acid or 240 ng/ml of zinc dipicolinate was added. Again, each of the cultures was grown in 25 ml of the deficient medium at 30° C. with continuous shaking for five hours. The mean increase in cell number was again calculated for the cultures and the results plotted in FIG. 2. As can be seen from FIG. 2, the growth promoter picolinic acid produced a 12% increase in cell growth rate under the conditions of the experiments, while the growth promoter zinc dipicolinate resulted in a 16% increase in growth rate, both in comparison to the control.

2. Growth In Complete Liquid Media

In a third series of experiments the complete medium, "DIFCO YM" was used, which contains a yeast extract, a malt extract, peptone, dextrose, and agar. Sufficient chromic trichloride (referenced as "chromic chloride") or chromic tripicolinate was added to 100 ml cultures of the "DIFCO YM" medium to reach a chromium concentration of 0.1 ng/ml in each, while sufficient picolinic acid was added to another culture to result in a picolinic acid concentration of 0.8 ng/ml. A 100 ml control culture of "DIFCO YM" medium did not receive any chromium or other added growth promoter. Baker's yeast was suspended in each of the 100 ml cultures to provide initial cell counts as follows:

Initial cell count of control = $3 \times 10^5$ cells/ml; initial cell count in culture to which picolinic acid added = $2.1 \times 10^5$ cells/ml; initial count in culture to which chromic chloride added = $3 \times 10^5$ cells/ml; initial cell count in culture to which chromic tripicolinate was added = $2.5 \times 10^5$ cells/ml.

The cultures were grown at 30° C. for 36 hours.

Figure 3A:
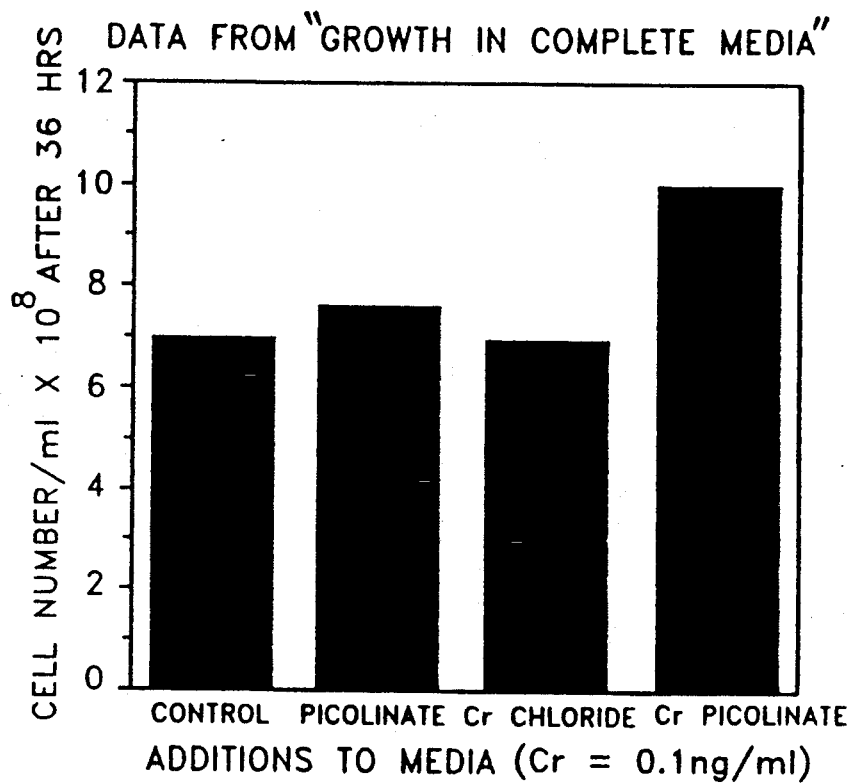
FIG. 3A illustrates the growth of a yeast culture in a complete medium, either in a control with no added growth promoter, with added growth promoters of the present invention, or with an added inorganic chromium salt.
Figure 3B:
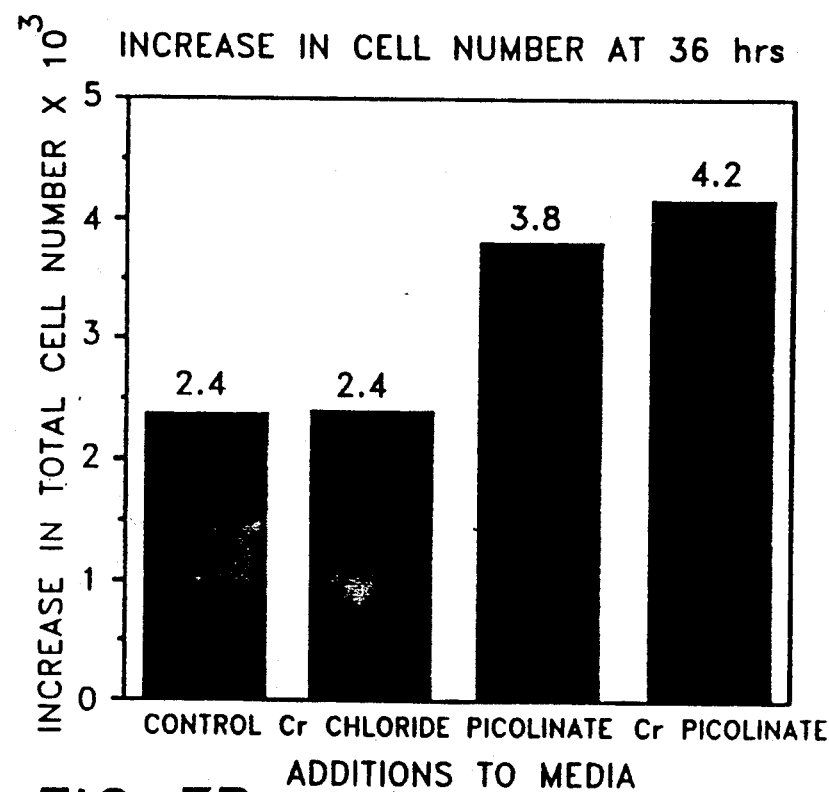
FIG. 3B illustrates the increase in growth found in each of the cultures as identified with FIG. 3 following a 36 hour incubation period.

The final cell number (mean, from a number of experiments) for each culture is illustrated in FIG. 3A. FIG. 3B illustrates the increase in cell number, as previously defined. As can be seen from FIG. 3A, the addition of the growth promoter picolinic acid, resulted in an increase of cell concentration which was approximately 56% greater than that of the control or the culture which received added chromic chloride. Similarly, addition of the growth promoter chromic tripicolinate resulted in an increase in cell concentration of approximately 74% greater than that in the control or the culture which received added chromic chloride.

3. Growth In Complete Solid Media

In another series of experiments the effect of both chromic chloride and the growth promoter chromic tripicolinate on the commercial yeast strain, Red Star Brand, was determined using a complete nutrient solid medium. The complete medium used was "DIFCO YM", with agar added to solidify it. A number of plates of solidified media were prepared containing either no additives (control), 8 ng of added chromium/ml (as chromic chloride or chromic tripicolinate) or 16 ng of added chromium/ml (as chromic chloride or chromic tripicolinate). The chromium compounds were added prior to pouring and solidification of the media. Yeast cells were taken from a solid slant ("DIFCO YM" medium) and diluted in an isotonic saline solution to $6 \times 10^8$ cells/ml. Cells were then transferred from the foregoing solution to the plates to provide $6 \times 10^5$ cells in total on each plate. Each plate was prepared in duplicate and all plates were incubated at 37° C. for 48 hours. The resulting colonies were counted with a standard colony counter and the results (mean, from a number of experiments) are plotted in FIG. 4.

Figure 4:
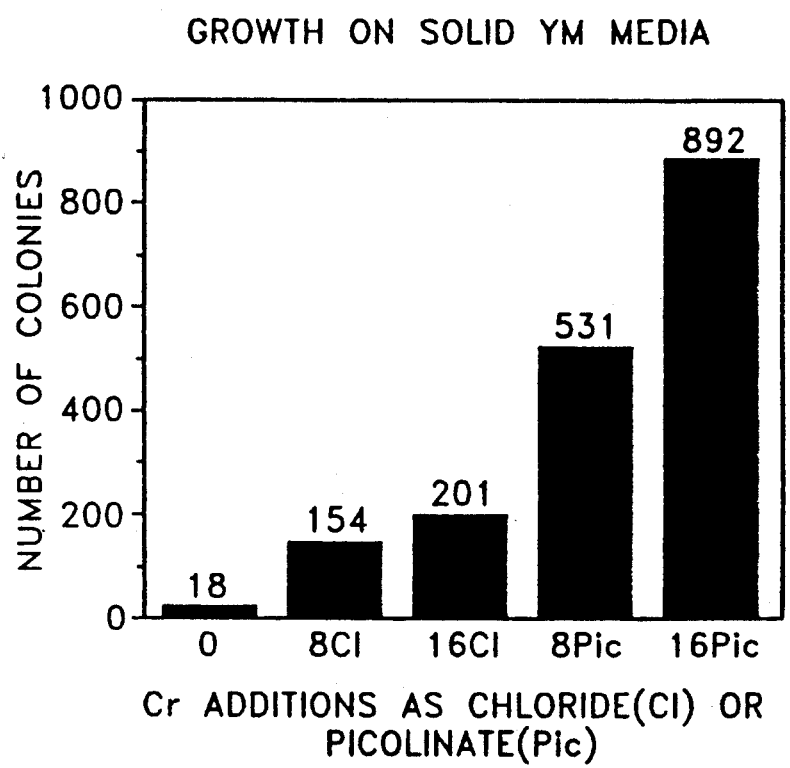
FIG. 4 illustrates growth of yeast cells on a solid complete medium with various amounts of added chromic chloride or chromic picolinate present.

It will be seen from FIG. 4 that those plates receiving 8 ng of chromium/ml (as the growth promoter chromic tripicolinate) exhibited an increase in total growth approximately 30 times greater than in the control, while those receiving 16 mg of chromium/ml (as the growth promoter of chromic tripicolinate) exhibited a total cell growth of almost 50 times greater than that in the control. Furthermore, the total cell growth of the plates receiving the chromic tripicolinate was approximately 4.5 to 5 times greater than (i.e., 450 to 500% of) growth in plates receiving a corresponding dosage of chromium in the form of chromic chloride.

In a further series of experiments, growth promoters were added to a potato dextrose agar ("PDA", sold under the name "BACTO-POTATO DEXTROSE AGAR" by Difco, Inc., Detroit, Mich., U.S.A.), a medium approved by various organizations for the detection and enumeration of yeasts. Cultures were prepared using a strain of baker's yeast different from that used in the preceding set of experiments. The growth promoters were added to PDA at the following concentrations (per ml PDA): 400 ng picolinic acid, 40 ng chromic tripicolinate, 40 ng tryptophan. The average yeast colony count was 11% to 18% greater than the count obtained with unsupplemented control cultures, as shown in the results below:

| ADDITIONS TO CULTURES | INCREASE IN YEAST CELL COUNT OVER CONTROL COUNT (%) |
|---|---|
| Picolinic Acid | 11 |
| Picolinic Acid + Chromic tripicolinate | 12 |
| Picolinic acid + Tryptophan | 18 |

Thus, chromic tripicolinate is also an extremely effective growth promoter in a solid culture medium.

4. Growth On Solid Starch Containing Media

Figure 5:
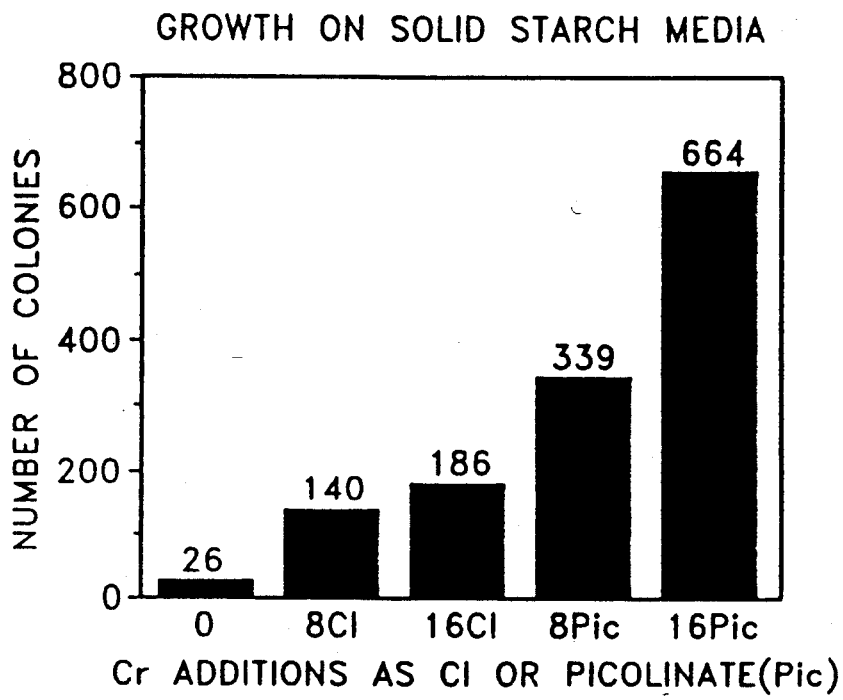
FIG. 5 is similar to FIG. 4 except that the medium contained starch rather than sugar.

The previous series of experiments with solid media, was repeated under the same conditions, except that a solid, starch containing complete medium was used instead of a sugar containing one. In particular, a "DIFCO" Starch complete medium was used, which contains a beef extract, soluble starch, and agar. The number of colonies counted (mean, from a number of experiments) on each of these plates after incubation at 37° C. for 48 hours is illustrated in FIG. 5. As can be seen from FIG. 5, the addition of 8 ng of chromium (as chromic tripicolinate) increased cell growth by a factor of about 9.4, while the addition of 16 ng of chromium (as chromic tripicolinate) increased the growth of the cells by a factor of about 25.5, both in comparison to the control having no added chromium. Likewise, the addition of 8 ng or 16 ng of chromium, both as chromic tripicolinate, produced cell growth that was about 2.4 times and 3.6 times (i.e., 240 and 360% of), respectively, the growth in those plates receiving corresponding added concentrations of chromium as chromic chloride. These experiments further demonstrate that chromic tripicolinate is an effective growth promoter in a solid starch-containing culture medium.

5. Growth On Solid Tryptone Containing Media

Figure 6:
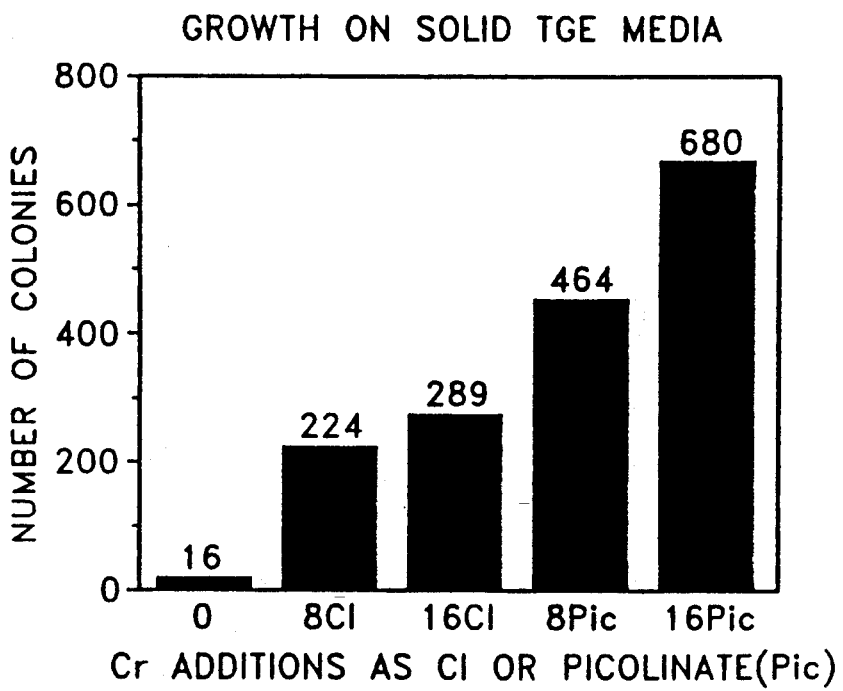
FIG. 6 is also similar to FIG. 4, except that a different solid medium, TGE, was used.

An additional series of experiments was performed, using the same parameters described above to generate the data of FIGS. 4 and 5, except that the solid medium used was a complete medium sold under the trademark "DIFCO TGE" (available from Difco Inc., Detroit, Mich., U.S.A.). "DIFCO TGE" contains a beef extract, tryptone, dextrose, and agar. The number of colonies on the plates after incubation, (mean, from a number of experiments) are plotted in FIG. 6. As will be seen from FIG. 6, the addition of 8 ng or 16 ng of chromium (as chromic tripicolinate) under the foregoing culture conditions, increased total cell growth by factors of approximately 34 and 23, respectively, in comparison to the control with no added chromium. Likewise, the addition of 8 ng and 16 ng of added chromium (in the form of chromic tricpicolinate), increased total cell growth by factors of greater than 2 and 2.3, respectively, in comparison to the plates with corresponding concentrations of added chromium in the form of chromic chloride. Thus, these experiments further illustrate that the addition of chromic tripicolinate to an otherwise normal, solid culture medium, can considerably enhance cell growth.

6. Growth of *E. coli*

Yeast are eukaryotes. A series of experiments was performed using the prokaryote *E. coli* bacterium. In these experiments a Nutrient Agar (available from Difco Inc.) containing either 65 ng or 130 ng of chromic tripicolinate/ml, and Nutrient Agar with no additions, were all first sterilized under standard conditions (15 psi steam, for 15 min.) Twenty milliliters of each of the foregoing medium was poured into petri dishes ("plates") and allowed to solidify. Each plate was streaked with $5 \times 10^5$ cells from a stock slant suspension of *E. coli*. Each plate was run in duplicate (for a total of 6 plates) and incubated at 37° C. The growth rate was determined by visual examination over a period of 24 hours. After six hours' incubation, a marked increase in the number of colonies was observed with the plates containing added chromic tripicolinate. Furthermore, after 24 hours, a visual examination of the plates indicated that those containing 65 ng of chromic tripicolinate had approximately 1.5 to 2 times (i.e., 150 to 200% of) the number of colonies as the control, while those plates which had received 130 ng of added chromic tripicolinate, had approximately 50% more colonies than those which had received only 65 ng of chromic tripicolinate. This, series of experiments illustrates that chromic tripicolinate is an effective growth promoter for prokaryote cells and, in particular, bacteria.

Various modifications and embodiments to the above-described invention, can be conceived by those familiar with the art. Accordingly, the present invention is not limited to the embodiments described in detail above but includes all such embodiments and variations.

We claim:

1. A microorganism growth media having no substantial quantity of active microorganisms, comprising:
   (a) a microorganism nutrient; and
   b) a growth promoter selected from picolinic acid and a metal picolinate, in an amount sufficient to produce an effective growth promoting concentration of picolinate up to about 400 ng/ml in said growth media.

2. A composition as defined in claim 1 promoting enhanced growth of a microorganism selected from yeast or bacteria wherein said microorganism nutrient is a saccharide.

3. A composition as defined in claim 1 wherein said growth promoter is selected from picolinic acid, and the chromic, zinc, iron, and manganese picolinates.

4. A composition as defined in claim 1, 2, or 3 wherein the growth promoter is selected from picolinic acid, chromic tripicolinate, and zinc dipicolinate.

5. A composition as defined in claim 1, 2, or 3 wherein the amount of the growth promoter is at least about 0.1 ng per gram of the medium.

6. A composition according to claim 1, 2 or 3 comprising a complete growth medium.

* * * * *